US012603166B2

(12) United States Patent
Arkoff et al.

(10) Patent No.: US 12,603,166 B2
(45) Date of Patent: Apr. 14, 2026

(54) PHARMACY SURVEILLANCE AND INTERVENTION SYSTEM FOR MONITORING, DETECTING AND PREVENTING NARCOTIC ABUSE

(71) Applicant: OneSource Solutions International, Inc., Sudbury, MA (US)

(72) Inventors: Harold Arkoff, Sudbury, MA (US); Vedran Jukic, Trieste (IT)

(73) Assignee: OneSource Solutions International, Inc., Sudbury, MA (US)

( * ) Notice: Subject to any disclaimer, the term of this patent is extended or adjusted under 35 U.S.C. 154(b) by 0 days.

(21) Appl. No.: 19/271,473

(22) Filed: Jul. 16, 2025

(65) Prior Publication Data

US 2026/0024639 A1 Jan. 22, 2026

Related U.S. Application Data

(60) Provisional application No. 63/672,862, filed on Jul. 18, 2024.

(51) Int. Cl.
| | |
|---|---|
| *G16H 20/10* | (2018.01) |
| *G16H 10/60* | (2018.01) |
| *G16H 40/20* | (2018.01) |

(52) U.S. Cl.
CPC ............. *G16H 20/10* (2018.01); *G16H 10/60* (2018.01); *G16H 40/20* (2018.01)

(58) Field of Classification Search
CPC ......... G16H 20/10; G16H 40/20; G16H 10/60
USPC ........................................ 705/2–3
See application file for complete search history.

(56) References Cited

U.S. PATENT DOCUMENTS

| | | | | |
|---|---|---|---|---|
| 7,585,680 B2 * | 9/2009 | Larson | ................... | G01N 33/94 |
| | | | | 436/171 |
| 7,765,106 B2 * | 7/2010 | Reardan | ................. | G16H 50/20 |
| | | | | 705/2 |
| 10,276,266 B1 * | 4/2019 | Piacentile | ............. | G16H 40/63 |
| 10,496,793 B1 * | 12/2019 | Lawrence | ............. | G16H 40/20 |
| 11,037,666 B1 * | 6/2021 | Benoit | ................... | H04L 41/16 |
| 11,289,179 B1 * | 3/2022 | Brown | ................... | G16H 10/60 |

(Continued)

*Primary Examiner* — Michael Tomaszewski

(74) *Attorney, Agent, or Firm* — IP Consulting Group; Michael Razavi; Alfred F Hoyte, Jr.

(57) ABSTRACT

A system and method for pharmacy-level surveillance of all prescription behaviors using one or more artificial intelligence (AI) agents integrated with real-time prescription records, refill timelines, prescriber data, patient histories, PDMP registries, and epidemiological signals. The system evaluates these inputs with configurable heuristics and machine-learned models to detect prescription abuse, public health risks, and equity or bias trends, including overlapping providers, dosage escalation, refill velocity, and prescriber clustering. When an anomaly is identified, a structured alert is routed to pharmacists, prescribers, or regulatory personnel through a secure, role-authenticated communication interface. Each system transaction and user outcome is captured by a Medical Data Governance (MDG) layer, providing cryptographic sealing, timestamping, and immutable ledger storage. In some embodiments, the audit log uses a blockchain-based distributed ledger. The system's feedback-driven, adaptive architecture enables analytic and policy modules to update automatically based on real-time outcomes, public health signals, and usage trends.

20 Claims, 5 Drawing Sheets

(56) References Cited

U.S. PATENT DOCUMENTS

| 11,361,381 | B1 * | 6/2022 | Lehmuth | G16H 20/10 |
| 11,721,430 | B1 * | 8/2023 | Schroeder | G16H 20/13 |
| | | | | 705/2 |
| 11,862,314 | B2 * | 1/2024 | Karbowicz | G16H 20/10 |
| 2003/0074225 | A1 * | 4/2003 | Borsand | G16H 20/10 |
| | | | | 705/3 |
| 2005/0048666 | A1 * | 3/2005 | Larson | G01N 33/70 |
| | | | | 422/400 |
| 2005/0102159 | A1 * | 5/2005 | Mondshine | G16Z 99/00 |
| | | | | 705/2 |
| 2008/0059226 | A1 * | 3/2008 | Melker | G16H 40/67 |
| | | | | 705/2 |
| 2010/0138237 | A1 * | 6/2010 | Reardan | G16H 10/60 |
| | | | | 705/2 |
| 2011/0173020 | A1 * | 7/2011 | Bailey | G06Q 10/10 |
| | | | | 382/218 |
| 2011/0288886 | A1 * | 11/2011 | Whiddon | G16H 80/00 |
| | | | | 705/3 |
| 2014/0012600 | A1 * | 1/2014 | Domesek | G16H 20/10 |
| | | | | 705/3 |
| 2014/0149128 | A1 * | 5/2014 | Getchius | G16H 50/20 |
| | | | | 705/2 |
| 2014/0257846 | A1 * | 9/2014 | Hermiz | G06Q 40/08 |
| | | | | 705/2 |
| 2014/0278479 | A1 * | 9/2014 | Wang | G06Q 10/10 |
| | | | | 705/2 |
| 2015/0019238 | A1 * | 1/2015 | Felt | G16H 20/10 |
| | | | | 705/2 |
| 2015/0235334 | A1 * | 8/2015 | Wang | G06F 21/50 |
| | | | | 705/2 |
| 2016/0004826 | A1 * | 1/2016 | Van Arkel | G06Q 40/08 |
| | | | | 705/3 |
| 2016/0180022 | A1 * | 6/2016 | Paixao | H04L 63/1408 |
| | | | | 705/3 |
| 2017/0270435 | A1 * | 9/2017 | Gallardo | G06Q 50/22 |
| 2018/0121620 | A1 * | 5/2018 | Bastide | G06F 16/334 |
| 2018/0285743 | A1 * | 10/2018 | Bringsjord | G06Q 30/0185 |
| 2018/0308569 | A1 * | 10/2018 | Luellen | G16H 20/10 |
| 2019/0096522 | A1 * | 3/2019 | Scriber | H04L 9/3247 |
| 2019/0156938 | A1 * | 5/2019 | Brunner | G16H 10/60 |
| 2020/0005213 | A1 * | 1/2020 | Clemens | G06Q 10/063114 |
| 2020/0051679 | A1 * | 2/2020 | Bostic | G16H 10/60 |
| 2020/0303047 | A1 * | 9/2020 | Bostic | G16H 50/50 |
| 2021/0020317 | A1 * | 1/2021 | Lillaney | G16H 70/40 |
| 2021/0043322 | A1 * | 2/2021 | Keni | G16H 30/40 |
| 2021/0104326 | A1 * | 4/2021 | Lorenzo | G16H 20/10 |
| 2021/0202106 | A1 * | 7/2021 | Bostic | G16H 50/20 |
| 2021/0295971 | A1 * | 9/2021 | Mills | G16H 40/67 |
| 2021/0319872 | A1 * | 10/2021 | Valentine | G16H 40/67 |
| 2021/0383292 | A1 * | 12/2021 | Samples | G16H 40/20 |
| 2024/0055110 | A1 * | 2/2024 | Shin | G16H 15/00 |

* cited by examiner

PHARMACY SURVEILLANCE AND INTERVENTION SYSTEM FOR MONITORING, DETECTING AND PREVENTING NARCOTIC ABUSE

CROSS-REFERENCE TO RELATED APPLICATIONS

This application claims the benefit of U.S. Provisional Application No. 63/672,862, filed on Jul. 18, 2024, titled "AI-Driven Pharmacy System for Monitoring and Preventing Narcotic Abuse", which is incorporated herein by reference in its entirety.

BACKGROUND OF THE INVENTION

Technical Field

The present invention relates generally to medical informatics and, more particularly, to systems and methods for surveillance of narcotic prescription patterns using artificial intelligence (AI). The invention specifically concerns pharmacy-embedded detection and intervention platforms for identifying prescription anomalies and coordinating resolution workflows among pharmacists, prescribers, and regulatory oversight entities through a secure, auditable communication framework.

Background of the Invention

The abuse of prescription narcotics remains a critical public health issue, driven by a combination of patient behavior, prescriber overuse, and fragmented data oversight. Current prescription monitoring programs (PMPs) are largely retrospective, often lack integration with local pharmacy systems, and fail to detect real-time abuse indicators such as overlapping prescriptions, dosage escalation, or cross-provider sourcing. Pharmacists are frequently placed in the position of final line-of-defense without access to timely or comprehensive data. Meanwhile, prescribers and regulators operate in silos, resulting in inconsistent intervention strategies and legal vulnerabilities. There remains a need for a pharmacy-facing platform that can proactively detect abuse risks, coordinate secure communication among stakeholders, and document intervention steps with full regulatory compliance.

SUMMARY OF THE INVENTION

The present invention provides a pharmacy-integrated AI platform for continuous surveillance of narcotic prescription behaviors. At its core, the system comprises one or more AI agents capable of analyzing real-time prescription events, patient medication histories, and prescriber behavioral trends. The system detects anomaly patterns using heuristics and machine learning techniques and generates structured alerts when defined risk thresholds are exceeded.

These alerts are routed to pharmacists and optionally to prescribers or regulators via a secure messaging interface. Each interaction is mediated through a Medical Data Governance (MDG) layer, which enforces access control, logs events immutably, and supports forensic traceability. The platform supports configurable intervention templates, allowing pharmacists or prescribers to document resolutions, override flags, or escalate cases. Alerts, decisions, and user responses are sealed cryptographically and stored in a compliance ledger that supports both regulatory reporting and root cause reconstruction.

The architecture is designed for compatibility with pharmacy management systems, electronic health records, and state PDMP registries, enabling broad adoption across institutions. It is deployable in retail, hospital, or virtual pharmacy settings and is optimized for low-latency clinical use.

A distinguishing feature of the invention is its synergistic, feedback-driven architecture, whereby every major analytic, policy, access, and reporting module is continuously and automatically adapted in response to real-time override outcomes, intervention feedback, external data sources—including prescription drug monitoring program (PDMP) inputs and epidemiological signals—and system usage trends. These adaptations occur without manual reprogramming and are cryptographically logged, enabling a self-optimizing, audit-ready system not achievable by prior art.

BRIEF DESCRIPTION OF THE DRAWINGS

The drawings presented herein show illustrative embodiments of the disclosure. They do not illustrate all embodiments. Other embodiments may be used in addition to or instead of the illustrative embodiments. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps. The drawings are not intended to depict every feature of every implementation nor relative dimensions of the depicted elements and are not drawn to scale.

DETAILED DESCRIPTION

Figure 1:
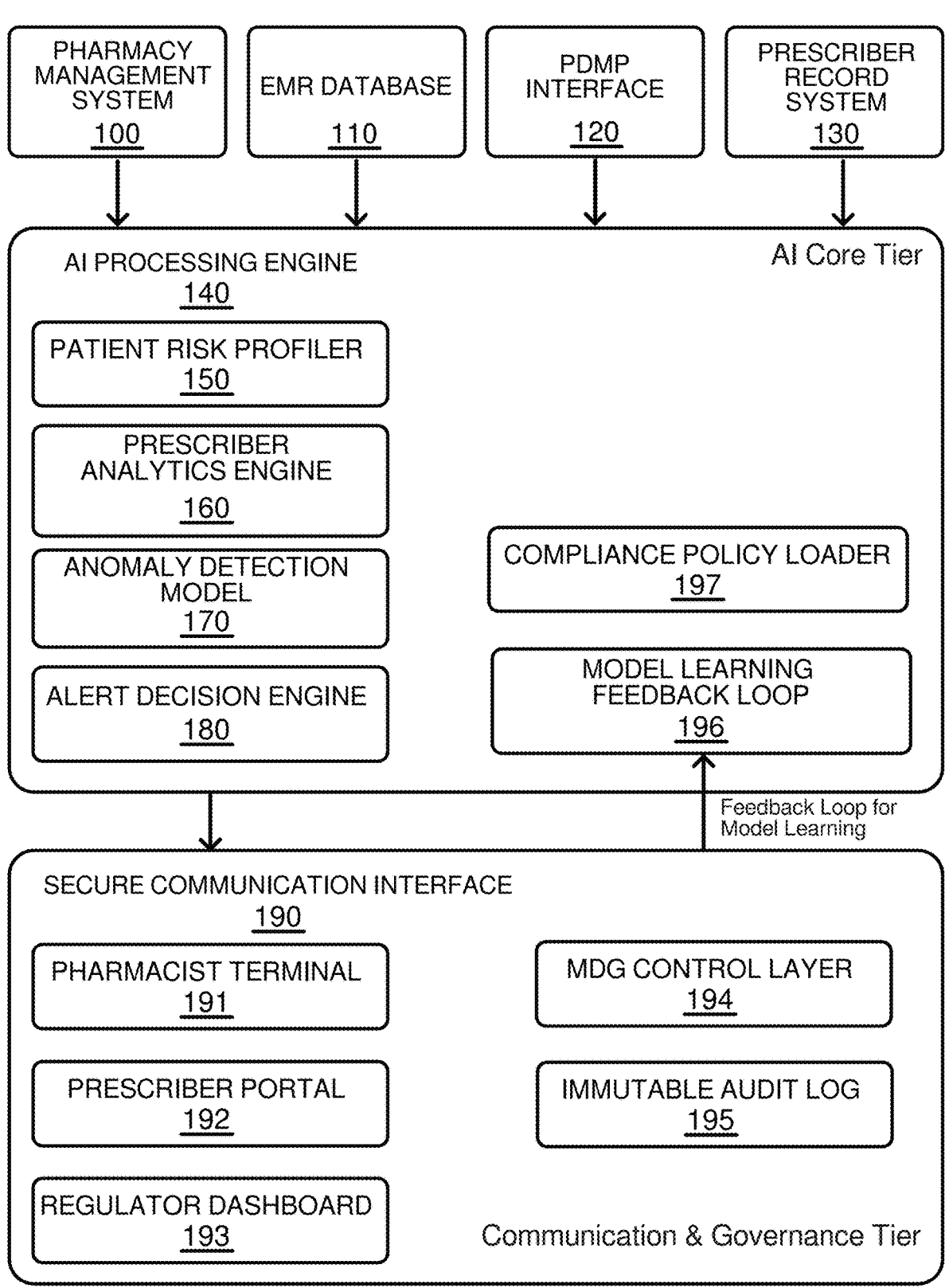
FIG. 1 is a high-level architectural diagram illustrating the multi-tiered structure of the pharmacy-integrated AI system.

In the following description, numerous specific details are set forth to clearly describe various specific embodiments disclosed herein. One skilled in the art, however, will understand that the subject matter of the present disclosure may be practiced without all of the specific details discussed below. In other instances, well-known features may not have been described so as not to obscure the invention with unnecessary detail regarding known features.

Definitions

Healthcare Information System: Any electronic system for managing patient, prescription, provider, or clinical data, including but not limited to pharmacy management systems, electronic medical records (EMRs), e-prescribing systems, and prescription drug monitoring programs (PDMPs).

Artificial Intelligence Techniques: Includes, but is not limited to, machine learning models (such as neural networks and ensemble models), statistical methods, heuristic logic, rule-based systems, and symbolic AI approaches.

Configurable Logic Module: Hardware, software, or a combination thereof, operable to implement detection criteria using rules, thresholds, heuristics, machine learning, or any combination thereof.

Detection Criteria: Any rule, set of rules, model, or parameter used by the system to identify high-risk, anomalous, or non-compliant prescription-related events, including but not limited to numeric thresholds, logical expressions, and pattern matching.

Credential-Binding Module: Any module or mechanism that associates an AI agent's authority to act or recommend actions with an authenticated human or institutional role, for purposes of delegation, audit, and compliance.

Tamper-Evident or Immutable Audit Log: A digital record of events, actions, or transactions in the system, implemented such that unauthorized alteration is either impossible or detectable, including (but not limited to) blockchain or hash-linked ledgers.

NCPDP-formatted Messages: Electronic messages structured according to the standards published by the National Council for Prescription Drug Programs (NCPDP), used in pharmacy and prescribing interoperability.

Gradient-Boosted Ensemble Model: A type of machine learning model that combines multiple weak predictive models to produce a stronger, more accurate prediction, frequently used for classification and regression tasks.

Blockchain-based Distributed Ledger: A digital database that records transactions in a decentralized, cryptographically secured, and tamper-resistant manner, providing proof-of-origin and auditability for stored events.

Artificial Intelligence Techniques (enhanced): Includes, but is not limited to, machine learning models (e.g. neural networks, tree ensembles, deep learning architectures), large language models (LLMs), foundation models, statistical methods, heuristic logic, rule-based and symbolic reasoning systems, knowledge graphs, and hybrid neuro-symbolic systems, as well as future forms of algorithmic or computational learning.

The invention relates to a pharmacy-integrated artificial intelligence (AI) platform configured to monitor, detect, and intervene in real time on potential instances of prescription narcotic misuse, prescriber deviation, and regulatory risk. The system is composed of a multilayered architecture that enables automated analysis, structured alerts, governance-level documentation, and feedback learning within a unified framework.

Referring first to FIG. 1, the system comprises three principal layers. An input tier receives structured data streams from a pharmacy management system 100, an electronic medical record (EMR) database 110, a prescription drug monitoring program (PDMP) interface 120, and a prescriber record system 130. These inputs serve as foundational sources of clinical, behavioral, and regulatory context.

The system may parse, interpret, and process prescription messages formatted according to the National Council for Prescription Drug Programs (NCPDP) standards, as received from external sources.

Prescription fill events are generated by the pharmacy management system and linked to historical patient data retrieved from the EMR database 110. Additional metadata, including narcotic history and cross-provider sourcing, is obtained through the PDMP interface 120. Data retrieved from external prescription drug monitoring programs (PDMPs) is used not only as input for real-time anomaly detection but also as comparative feedback to validate and, if necessary, automatically adapt internal AI risk models and detection logic. Discrepancies between PDMP alerts and internal detections may trigger retraining or recalibration of model parameters, enhancing system reliability and regulatory alignment. The prescriber record system 130 contributes analytics on physician-specific behaviors.

This input data is processed by an AI engine 140 depicted in the central region of FIG. 1. The AI processing engine 140 performs coordinated evaluation across several internal modules, including a patient risk profiler 150, a prescriber analytics engine 160, and an anomaly detection model 170. In certain embodiments, the risk scoring engine 150 utilizes a gradient-boosted ensemble model trained on a labeled dataset of known prescription misuse events. These modules analyze refill frequency, dosage escalation, prescriber diversity, and trend-based deviations. Upon identification of a suspicious pattern, the alert decision engine 180 executes policy-based logic to determine whether an alert should be issued. In certain embodiments, the output of the patient risk profiling module is used to dynamically update and tune the detection parameters, weighting, or rules applied by the prescriber analytics engine in real time, and vice versa. This reciprocal adaptation enables the system to synergistically refine risk scoring and detection logic as new patterns emerge, producing more accurate and context-aware intervention recommendations. The alert decision engine 180 may include a configurable logic module to implement detection criteria, which can include, but are not limited to, rules, thresholds, heuristics, or learned decision logic. The decision is routed through a secure communication interface, which supports transmission to one or more designated recipients, including pharmacists, prescribers, and regulators.

Figure 2:
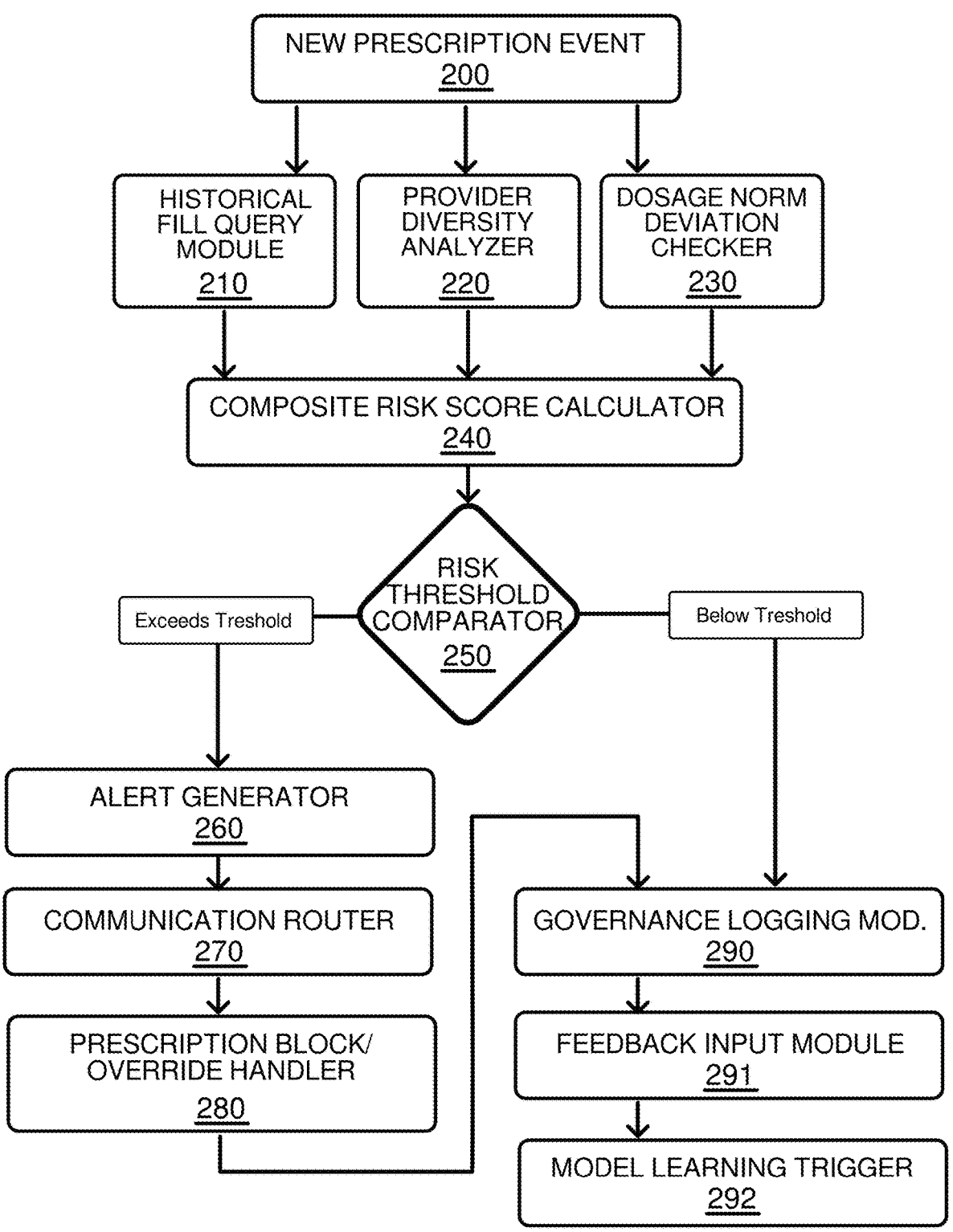
FIG. 2 is a logical flowchart depicting the patient risk scoring process.

As further illustrated in FIG. 2, the alert workflow is initiated upon receipt of a qualifying new prescription event. The system activates modules that evaluate historical refill behavior, prescriber diversity, and dosage deviation from regional norms. Each of these risk signals is quantified and combined by a composite risk score calculator. The resulting score is evaluated against a configurable threshold defined by institutional policy. If the score exceeds this threshold, the alert generator constructs a structured message that is routed to authorized endpoints. The communication router delivers this alert in real time to the pharmacist-of-record or to a prescriber or regulatory body as dictated by policy. Actions taken in response to the alert, including block, override, or escalation, are processed through a governance logging module, which records the transaction into a sealed ledger. Upon generation of a high-risk alert, the system may temporarily suspend prescription dispensing pending manual review or override by authorized personnel. Confirmed outcomes are optionally submitted to a model feedback module for the purpose of refining future predictions.

At every stage, the system analyzes feedback from overrides and interventions, as well as external signals, using these insights to update risk score calculation logic, detection criteria, and alert thresholds for future transactions. This creates a continuously adaptive workflow wherein the risk models, policy logic, and intervention templates evolve with system usage, new threats, and public health trends—all with cryptographically assured auditability. Every time an anomaly is detected—such as high-frequency fills or overlapping prescriptions, the system immediately incorporates the event and any subsequent override or intervention outcome as feedback, using it to automatically refine detection model weights and alert thresholds. In this manner, the detection system becomes increasingly precise with continued operation.

Figure 3:
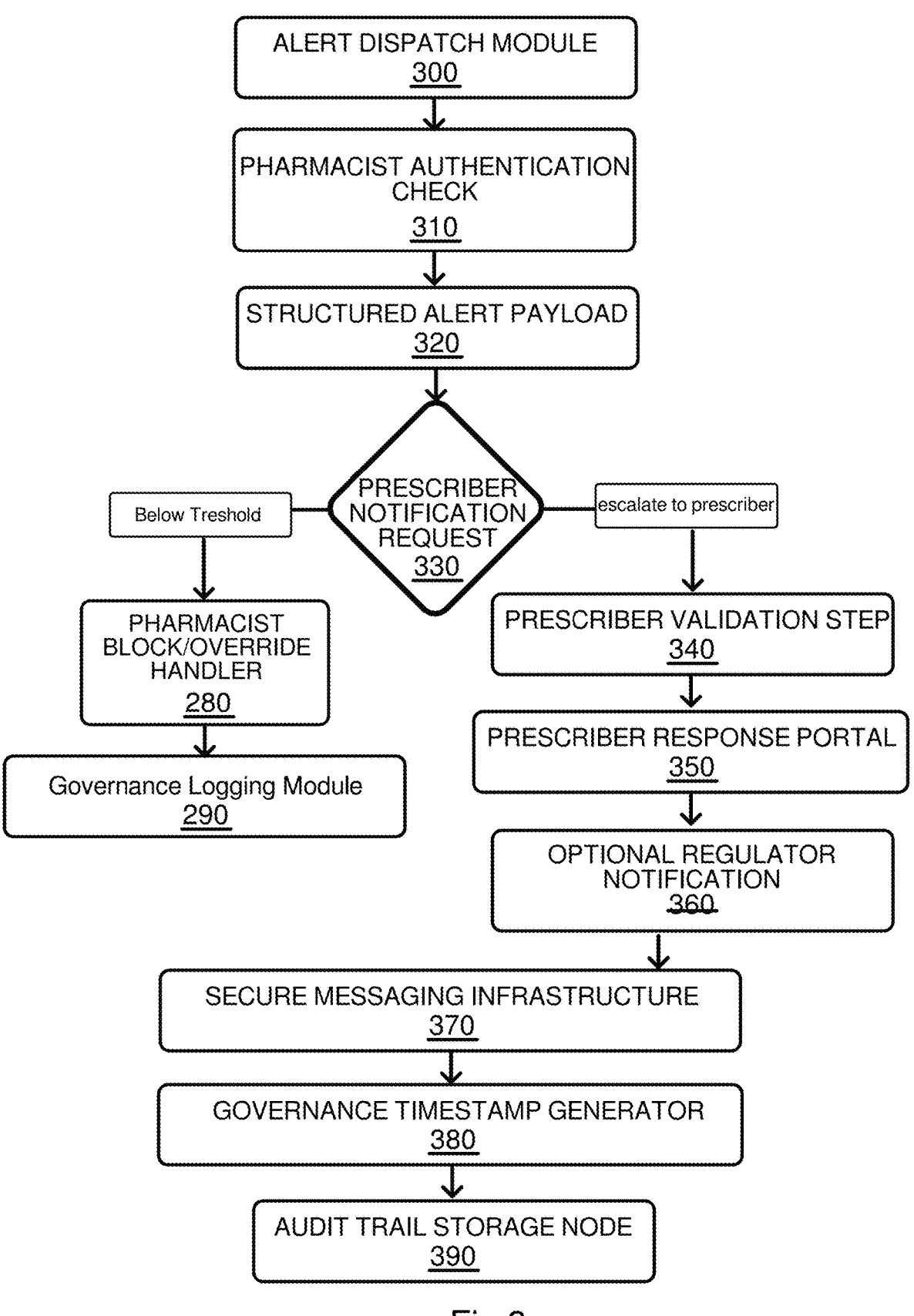
FIG. 3 is a schematic representation of the structured communication workflow.

The communication topology is shown in FIG. 3. The alert dispatch module is responsible for delivering structured payloads to verified users. Each message undergoes a role-based authentication check before being routed to a recipient terminal. Pharmacists receive an alert describing the risk signature and are presented with a menu of possible responses. If they elect to involve the prescriber, a digitally signed notification is generated and delivered to the appropriate provider through a prescriber response portal. The provider may acknowledge the alert, override it with rationale, or request additional clarification. In certain cases, institutional policy may require passive or active notification of a regulatory official, which is facilitated through a secure messaging infrastructure. Each message is signed, time-stamped, and logged within the governance architecture.

Role-based access permissions, and the required forms or templates for documenting overrides and interventions, are dynamically recalibrated by the system in response to recent override feedback, observed patterns of intervention outcomes, and updates to institutional policy. This ensures that access and compliance documentation remain aligned with real-world usage trends and regulatory demands.

Figure 4:
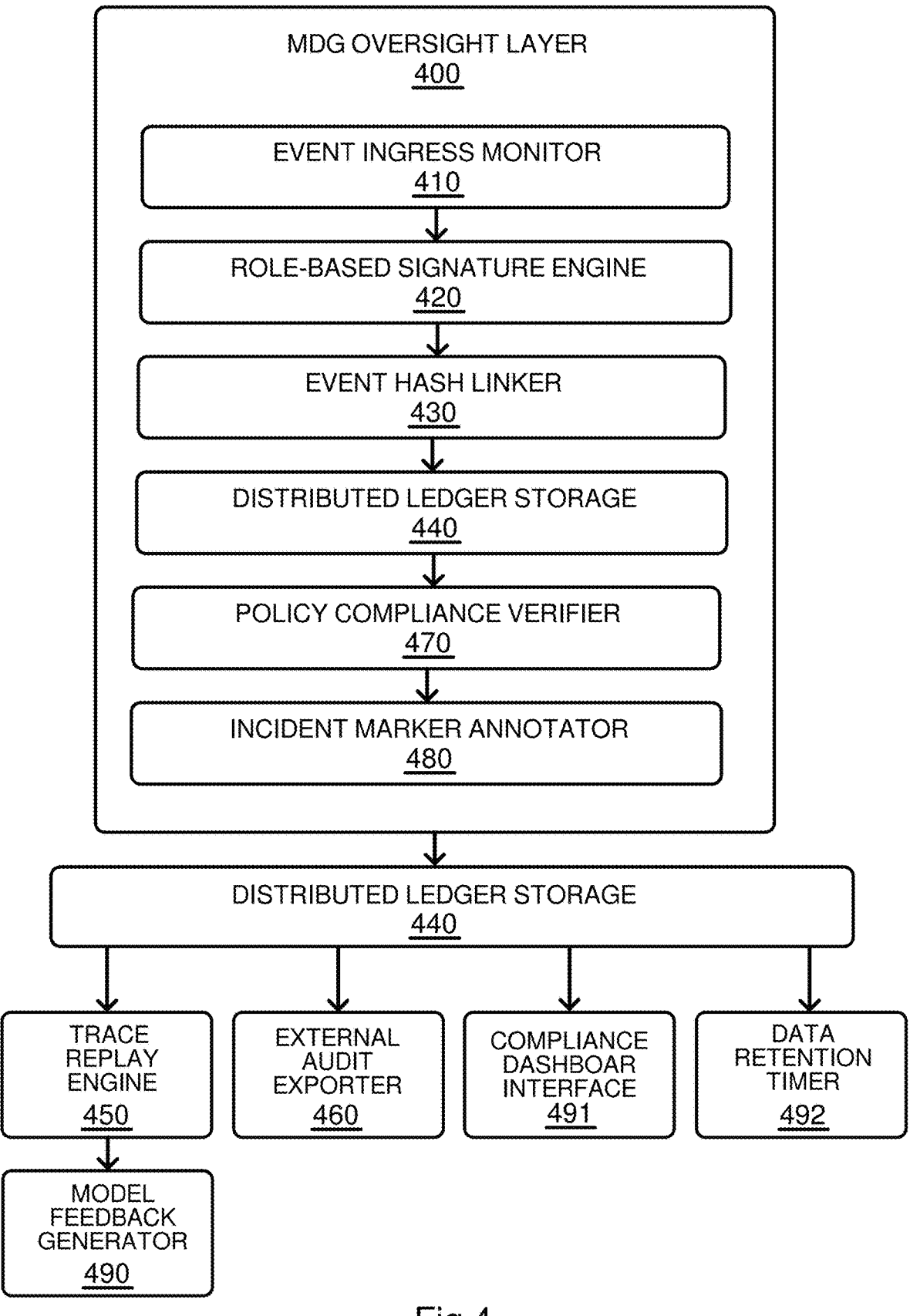
FIG. 4 is a system architecture diagram showing the Medical Data Governance (MDG) layer, which ensures event immutability, compliance tagging, audit replay, and sealed ledger storage.

Governance traceability is managed by a dedicated medical data governance layer illustrated in FIG. 4. This subsystem continuously monitors transactional ingress, applies cryptographic role-based signatures to each event, and enforces immutability through chained hash linkage. The MDG oversight layer verifies compliance with policy, generates tamper-evident timestamps, and stores each event in a distributed ledger. Authorized auditors may reconstruct complete trace sequences using a trace replay engine, or export signed, evidentiary bundles for legal or institutional review. Confirmed alerts and overrides are further harvested into a feedback generator, which produces retraining datasets for use in model updating. A data retention timer ensures that event histories are managed in accordance with jurisdictional rules and institutional governance mandates.

In addition to cryptographically logging all user actions, the governance module is configured to record every adaptation to detection logic, alert thresholds, access control settings, and reporting parameters, with time-stamped, role-signed, and immutable entries. This creates a comprehensive, auditable record of both user interventions and system self-optimization events.

The invention is designed to interoperate with a broad spectrum of healthcare technologies. It supports integration with PDMP registries, pharmacy management systems, and electronic medical record systems through standards-based interfaces. Communication payloads are secured via encryption and are compliant with healthcare privacy frameworks such as HIPAA. The platform can be deployed in physical pharmacy locations, hospital dispensaries, or virtual pharmacy networks, and operates under latency constraints suitable for live clinical decision-making. All alert generation, override resolution, and governance event recording occurs within the window of a single prescription transaction.

The system thereby enables not only the automated detection of narcotic misuse signals but also provides a legally defensible, traceable, and auditable workflow for pharmacist and prescriber intervention. The embedded governance layer ensures compliance with state and federal oversight requirements, while the AI modules continuously adapt to emergent risk patterns through model retraining anchored in validated historical outcomes.

Agentic AI Execution Framework

The present system further includes an agentic artificial intelligence (AI) execution framework, wherein the AI modules function as delegated agents acting within defined institutional boundaries. Each AI decision, including the issuance of alerts, is constrained by a policy grammar comprising rules that encode dosage thresholds, refill intervals, cross-provider sourcing heuristics, and regional prescribing norms. The delegation framework may utilize a credential-binding module to enforce AI agent authority limitations based on authenticated user roles and institutional rulesets. The AI agents do not operate autonomously but are bounded by rule-expressive grammars that dictate legal and clinical context.

In this agentic framework, each action initiated by the AI—such as generating an alert or withholding a prescription recommendation—is legally attributable to a predefined institutional policy. Overrides by human actors, including pharmacists or prescribers, must occur through a structured interface that requires justification bound to the actor's role and credential. These justifications are captured in a tamper-evident governance envelope and linked to the original AI action to preserve causal integrity.

The policy-constrained execution engine, credential delegation framework, and justification capture logic are all configured to be dynamically updated based on real-time analysis of system-wide override patterns, intervention results, and external signals (such as outbreak data). Updates to policy grammars, credential boundaries, and override rationale requirements occur automatically and are cryptographically recorded in the governance layer for audit and compliance.

Additionally, each agentic decision is recorded with its originating rule trace, enabling authorized auditors to reconstruct the rationale under which a given alert or recommendation was issued. A replay engine supports time-indexed traversal of AI reasoning steps, including decision forks, threshold evaluations, and policy invocation paths. This allows downstream adjudication in regulatory, clinical, or legal forums.

The agentic execution framework thereby ensures that all AI outputs are legally traceable, human-intervenable, and reconstructible, satisfying institutional and regulatory requirements for safe, explainable, and accountable AI use in clinical pharmacovigilance workflows.

Epidemiological Signal Integration for Agentic Governance

The system optionally incorporates an external epidemiological signal ingestion layer configured to receive real-time alerts from third-party outbreak surveillance platforms, such as BlueDot 2.0. These external data streams may include regional pathogen detection reports, symptom cluster alerts, or other public health indicators indicative of infectious disease emergence.

The policy-constrained execution engine is configured to interpret these signals as modulating parameters in the alert generation process. Specifically, prescription alert thresholds may be dynamically tightened or relaxed based on outbreak signal intensity or geospatial congruence. For example, a narcotic refill threshold may be tightened during a flu outbreak to mitigate risk of misuse or temporarily relaxed to accommodate regional patient influxes in emergency scenarios.

Overrides performed by prescribers or pharmacists during periods of active outbreak may be annotated with structured epidemiological context, including outbreak tag identifiers, temporal scope, and jurisdictional metadata. These annotations are preserved in the structured justification capture module and are embedded in the tamper-evident audit trail for future analysis.

All adjustments made in response to outbreak conditions are recorded within the agentic replay trace engine, which ensures retrospective visibility into the influence of epidemiological signals on AI decision-making. This integration enables institutions to justify or contest specific AI outputs in light of dynamic public health conditions, while maintaining agentic traceability, explainability, and compliance alignment.

Extension to Broader Clinical Pharmacovigilance Domains

While the present disclosure provides detailed examples in the context of narcotic and opioid prescription surveillance, the disclosed system is designed to function across a wide range of clinical pharmacovigilance domains. Specifically, the policy-constrained execution engine, override grammar logic, and agentic audit trace functionality may be applied to non-narcotic pharmaceutical classes including, but not limited to, antibiotics, antipsychotics, anticoagulants, immunosuppressants, hormone therapies, and high-risk cardiometabolic agents. In each such domain, alert thresholds and override interfaces may be governed by therapeutic-specific grammars reflecting pharmacodynamic sensitivity, dosage escalation risk, and population-level behavioral compliance metrics.

The outcomes of specialty medication interventions—such as approvals, denials, or overrides—are analyzed as feedback, and the system automatically updates threshold logic and preauthorization criteria for subsequent cases involving similar medications or clinical contexts. Each preauthorization and override event is cryptographically logged for traceable auditability.

Furthermore, the system may be configured to monitor preventive care adherence, including the tracking of vaccination schedules, timing conflicts with live attenuated vaccines, and institutional mandates for pandemic response protocols. Justifications captured during pharmacist or prescriber override actions in these domains may be role-specific and recorded in the same tamper-evident audit trace as disclosed herein.

This extended applicability ensures that the invention may serve as a modular surveillance and governance layer not only for narcotic risk mitigation, but also for broader compliance oversight, behavioral adherence auditing, and AI-based decision accountability across institutional and public health contexts.

FIG. 1 illustrates a high-level system architecture for the AI-driven pharmacy surveillance system of the present invention. The architecture is composed of three logical tiers: (1) an Input Tier that receives prescription-related data from pharmacy and clinical systems; (2) a centralized AI Core Tier that processes, analyzes, and detects potential narcotic abuse; and (3) a Communication and Governance Tier responsible for alerting, intervention logging, and compliance enforcement.

As mentioned above, the Input Tier collects and streams structured data from pharmacy management software, electronic medical records (EMRs), prescriber profiles, and state PDMP databases. This data enters the AI Core Tier, where it is parsed, correlated, and analyzed using both heuristics and trained ML models. Modules include a Patient Risk Profiler 150, a Prescriber Analytics Engine 160, a Statistical Anomaly Detector 170, and an Alert Decision Engine 180. A compliance policy loader 197 retrieves institutional policy rules.

If an alert condition is met, the system transitions to the Communication and Governance Tier, where an appropriate person, typically a pharmacist, is notified. Users interact with the platform through secure, role-authenticated terminals, including a pharmacist terminal 191, a prescriber portal, which includes one or more devices for network communication. All interactions, alerts, overrides, and responses are captured by the Medical Data Governance (MDG) Control Layer 194, which applies cryptographic sealing, role-signed attestations, and immutable ledger storage. A feedback loop 196 provides outcome-confirmed signals back to the AI Core for model refinement.

FIG. 2 provides a logical flowchart representing how the system performs patient-specific risk scoring for narcotic misuse and determines whether to trigger a real-time alert. The workflow is initiated when a new narcotic prescription is entered into the pharmacy system.

Upon detection of this trigger event, the AI agent retrieves and evaluates several key risk signals: the patient's historical refill behavior, the number and diversity of prescribers, and the deviation of the current dosage from therapeutic norms. These inputs are scored and aggregated by a composite risk calculator. If the resulting score exceeds a policy-defined threshold, the system issues an alert.

The alert is then routed through a secure messaging interface to the appropriate stakeholders. Regardless of whether an alert is issued, all processing outcomes are recorded in a governance audit trail. Confirmed outcomes are also looped back into the model as feedback for future refinement.

FIG. 3 illustrates the multi-party communication workflow initiated when an abuse-risk alert is generated. This figure defines the message routing logic and authentication steps between the pharmacy, prescriber, and optional regulatory reviewer. The system enforces role-based communication privileges to ensure that each message is delivered only to authenticated and appropriate participants.

Upon generation of an alert, the system identifies the pharmacist responsible for the fill event and delivers a structured message including the risk trigger, supporting data, and available resolution options. If the pharmacist elects to notify the prescriber, a digitally signed request is generated and routed through the secure interface. Prescribers may respond with agreement, override rationale, or request clarification.

In flagged cases or by institutional policy, a regulator may be looped in, either passively for audit or actively to adjudicate disputes. Each interaction is time-stamped, role-signed, and recorded in the governance ledger.

FIG. 4 depicts the internal reference architecture of the system's Medical Data Governance (MDG) layer. This component serves as the integrity backbone of the platform, ensuring that every alert, message, override, and outcome is recorded in a tamper-evident, role-signed, and chronologically linked audit trail.

The MDG layer intercepts all transactions—whether automated or user-initiated—and applies a governance envelope that includes timestamping, signature stamping, and policy compliance tagging. Entries are hashed and linked to previous entries to enforce immutability. These records are stored redundantly in a distributed ledger to ensure compliance durability and support regulatory audit.

The system allows event replay by authorized personnel and exports digitally sealed evidence bundles for institutional review, liability defense, or post-incident root cause analysis. Confirmed alerts and confirmed overrides are harvested into a training stream for future model evolution.

Figure 5:
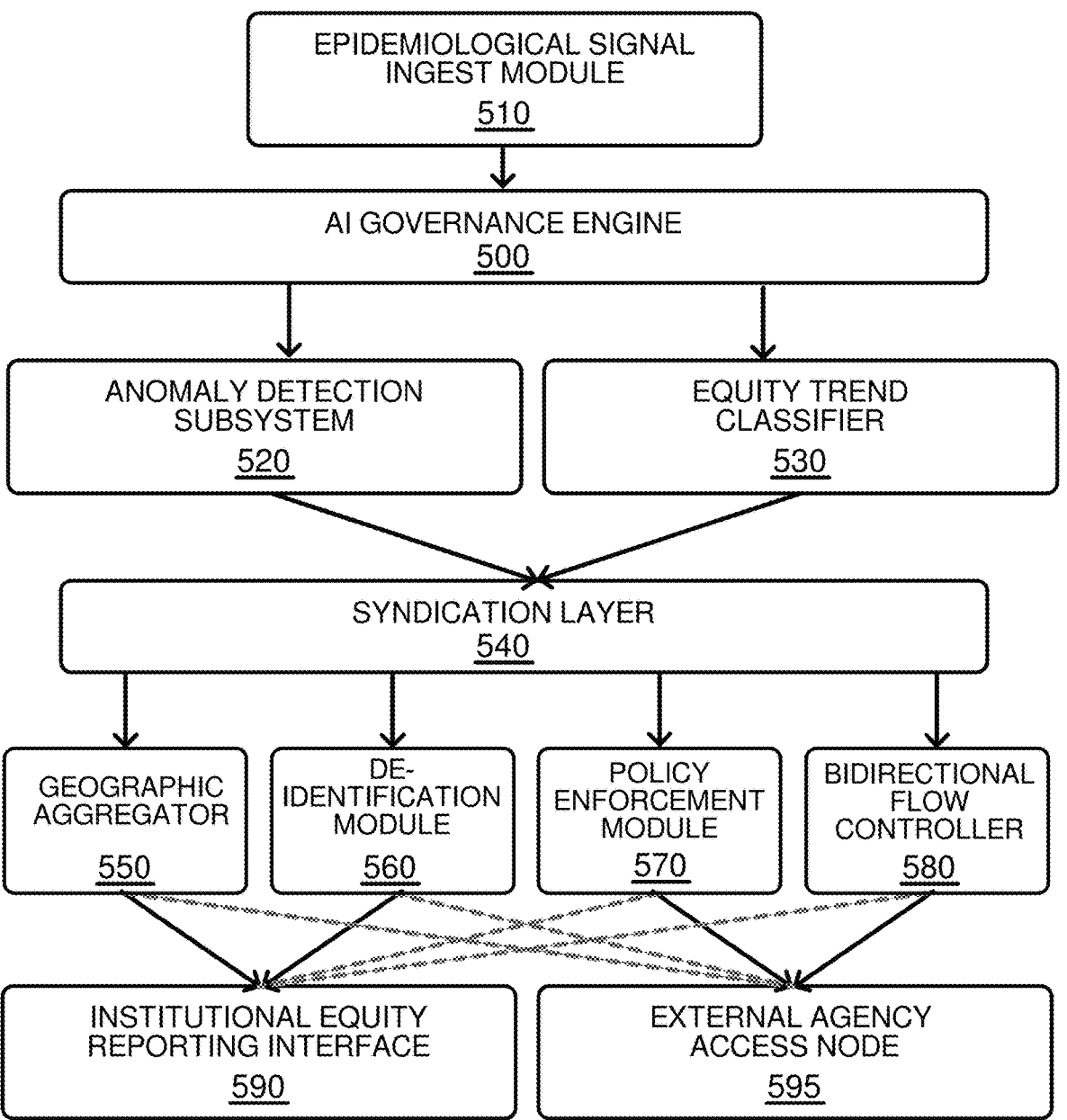
FIG. 5 illustrates a public health alert syndication and feedback layer.

FIG. 5 illustrates a public health alert syndication and feedback layer that complements the system's internal governance engine. The AI Governance Engine (500) ingests epidemiological signals via the Epidemiological Signal Ingest Module (510), which receives real-time alerts such as pathogen cluster warnings or outbreak notifications. These inputs are analyzed by the Anomaly Detection Subsystem (520), which identifies statistically significant deviations in prescribing behavior across providers, pharmacies, and patient subpopulations. The Equity Trend Classifier (530) further analyzes demographic and geographic patterns, flagging disparities in override behavior, prescription denial frequency, or alerting rates by ZIP code or insurance class.

Insights derived from this analysis are routed to the Syndication Layer (540), which prepares outbound public health feedback. The Geographic Aggregator (550) summarizes prescription and override data by region, while the De-Identification Module (560) ensures that any patient or provider information is obfuscated prior to transmission. The Policy Enforcement Module (570) applies institutional authorization constraints, ensuring all outbound transmissions comply with governance policies. The Bidirectional Flow Controller (580) manages both the inbound signal ingestion and outbound syndication, maintaining a continuous epidemiological feedback loop.

The system continuously analyzes override and reporting trends, and it automatically adapts analytics thresholds and reporting logic to ensure ongoing, real-time equity and bias detection. All such analytic logic changes, triggers, and the rationale for reporting are cryptographically recorded and available for compliance and institutional review.

The Institutional Equity Reporting Interface (590) allows internal compliance or diversity committees to monitor bias metrics. Simultaneously, the External Agency Access Node (595) serves as a secure transmission point to state-level health exchanges, CDC partners, or regulatory dashboards. This end-to-end infrastructure ensures actionable public health insight flow, tightly coupled with traceable institutional governance.

The invention claimed is:

1. A computer implemented system for monitoring and governing prescription events to detect and intervene in potential prescription-related misuse, non-compliance, or regulatory non-conformance, comprising:

(a) one or more artificial-intelligence (AI) agents configured to:

(i) receive structured, real-time prescription and dispensing data from at least one healthcare information system, the data comprising structured prescription and dispensing attributes associated with a patient and a prescribed medication;

(ii) access patient health or medication history information and provider behavioral patterns;

(iii) apply machine-learning or statistical models to compute a risk score for each prescription event based on patient-specific attributes; and (iv) compare the computed risk score with a configurable threshold defined by institutional policy to identify candidate alerts for potential non-compliance;

(b) a secure communication interface configured for transmitting candidate alerts or intervention requests to authorized clinicians or regulatory recipients and for receiving override justifications or intervention feedback;

(c) a policy-governance module configured to apply a stored policy grammar that encodes dosage caps, dispensing intervals, or cumulative sourcing limits to determine whether issuance of a candidate alert is permitted under applicable jurisdictional or institutional constraints, and, when a violation is detected, to temporarily suspend prescription dispensing or alert issuance pending manual review or override by an authorized clinician or regulator;

(d) a medical-data governance and audit module configured for cryptographically recording, in a chained tamper-evident log, each prescription event, computed risk score, applied policy grammar, and reviewer action for regulatory compliance and retrospective analysis; and (e) a configurable logic module configured to automatically update detection criteria, policy thresholds, and machine-learning parameters of the AI agents based on reviewer feedback and override outcomes, thereby providing a feedback-driven adaptation of the system, wherein the feedback updates are cryptographically linked in the audit log, (f) an omission-event detection engine configured to evaluate, for each prescription event, whether one or more policy-defined required system actions—including required acknowledgments, required reviews, required confirmations, or required override entries specified by the institutional policy grammar—are missing or not completed within a policy-defined time window, thereby generating a policy-defined omission event;

(g) an authorization-state controller configured to enforce, via a machine-executable state-transition model, a prescription-authorization state for each prescription event, wherein execution of a prescription event or a corresponding dispensing action is automatically prevented or suspended until the cryptographically chained audit log contains a policy-verified entry indicating completion of all required system actions or an authorized override of the omission event; and (h) a cryptographic validation engine configured to verify, prior to enabling any state transition that clears an alert, resolves an omission event, or authorizes dispensing, that a corresponding audit-log entry includes: (i) a hash referencing at least one prior entry in the log, (ii) a digital signature associated with the authenticated role of the reviewer, and (iii) a timestamp satisfying the institutional policy grammar;

Wherein the system controls authorization states for prescription events such that execution of a prescription or dispensing action is contingent upon cryptographically verifiable satisfaction of policy-defined system requirements, thereby providing a technical improvement in secure healthcare data processing through traceable, policy-constrained, and tamper-resistant operation of an AI-driven prescription-monitoring system.

2. The system of claim 1, wherein the AI agents comprise both a patient risk profiling module and a prescriber analytics engine, wherein detection results from either module, upon exceeding pre-defined thresholds, trigger dynamic updates to the other module's risk calculation parameters and detection logic, enabling reciprocal, real-time adaptation to emerging risk trends.

3. The system of claim 1, wherein the secure communication interface enforces role-based access controls for pharmacists, prescribers, and regulatory personnel, wherein the type and scope of access permissions, as well as required documentation for overrides or interventions, are dynamically adjusted based on analysis of recent override feedback and evolving institutional policy.

4. The system of claim 1, wherein the anomaly detection models identify high-frequency fills, overlapping prescriptions, and cross-provider sourcing patterns, wherein each new anomaly detection event is used to further refine, in real time, the model's feature weights and detection thresholds through a continuous, automated learning process incorporating feedback from override and intervention data.

5. The system of claim 1, wherein the medical data governance module generates hash-linked entries for forensic auditability and supports blockchain-based ledger storage, wherein every adaptation to detection logic, alert thresholds, or access policies is cryptographically time-stamped, role-signed, and retrievable for regulatory inspection or legal discovery.

6. The system of claim 1, wherein the system is integrated with a state prescription drug monitoring program (PDMP) via an application programming interface (API), wherein data retrieved from the PDMP is used both as an input for real-time anomaly detection and as feedback to adapt AI risk models and detection parameters, enabling external data-driven adjustment of internal logic.

7. The system of claim 1, further comprising a specialty medication classification module for applying enhanced threshold logic and preauthorization audit capture for high-cost or immunomodulatory therapies, wherein outcomes of specialty medication interventions are used to adapt the threshold logic for subsequent cases, and each preauthorization and override event is recorded in the governance module for traceable audit.

8. A computer-implemented method for detecting prescription-related misuse or non-compliance events and facilitating real-time intervention, the method comprising:

(a) receiving, in real time, structured prescription and dispensing data from at least one healthcare information system, the data comprising structured prescription and dispensing attributes associated with a patient and a prescribed medication;

(b) accessing patient health or medication history information and healthcare-provider behavioral or prescribing data;

(c) determining, by one or more processors executing an artificial-intelligence model, a risk score for each prescription event based on patient-specific attributes;

(d) comparing the computed risk score with a configurable threshold defined by institutional policy and applying a stored policy grammar that encodes dosage caps, dispensing intervals, or cumulative sourcing limits to determine whether issuance of a candidate alert is permitted under applicable policy constraints;

(e) when the candidate alert violates the policy grammar, temporarily suspending prescription dispensing or alert issuance pending manual review or override by an authorized clinician or regulator;

(f) recording, in a cryptographically chained tamper-evident audit log, information identifying the prescription event, the computed risk score, the applied policy grammar, and any reviewer action; and (g) identifying a policy-defined omission event by determining that one or more required system actions-including required confirmations, required reviews, or required override entries specified by the institutional policy grammar—have not been completed within a policy-defined time window;

(h) recording each omission event, required action, reviewer response, threshold update, and system adaptation as a cryptographically linked entry in the audit log;

(i) enforcing, via a machine-implemented authorization-state controller, a state in which prescription dispensing, alert clearance, or completion of a prescription-authorization state is automatically prevented until the audit log contains a cryptographically verifiable entry documenting completion of all required system actions or an authorized override; and (j) continuously analyzing override and intervention outcomes to update and adapt risk-score calculation logic, detection criteria, and alert-generation thresholds, enabling feedback-driven adaptation without manual reprogramming;

wherein performance of the method provides a technical improvement in secure healthcare data processing by ensuring traceable, policy-constrained, and tamper-resistant operation of an AI-driven prescription-monitoring workflow.

9. The method of claim 8, wherein the collecting step further comprises parsing National Council for Prescription Drug Programs (NCPDP)-formatted messages, wherein parsed data is automatically mapped to risk models, and observed discrepancies or outlier values are used to adapt parsing logic and risk signal weighting for future events.

10. The method of claim 8, wherein the abuse risk score is computed using a gradient-boosted ensemble model trained on labeled misuse data, wherein each confirmed intervention or override is incorporated into a continuously retrained dataset, and the alert generated comprises a structured rationale citing specific risk signals and adaptive thresholds.

11. The method of claim 8, wherein the routing step is performed via a secure, encrypted, HIPAA-compliant channel, and further comprising collecting pharmacist or prescriber feedback, analyzing feedback trends in real time, and using them to retrain the AI model and adjust alert thresholds and routing logic.

12. The method of claim 8, wherein the governance log includes timestamps, device identifiers, authenticated user roles, and is retrievable for regulatory inspection or legal discovery, and further wherein every system update, intervention, override, and logic adaptation is cryptographically linked for complete lifecycle traceability.

13. The method of claim 8, further comprising suspending prescription dispensing pending resolution based on alert criteria, wherein suspension and override outcomes are used as realtime data to adapt future alerting thresholds and intervention logic.

14. A system for agentic artificial-intelligence (AI) execution in clinical pharmacovigilance, comprising:

(a) a policy-constrained execution engine configured to receive structured prescription and dispensing data from at least one healthcare information system and to interpret and update institutionally defined grammars for prescription-alert generation;

(b) a delegation framework assigning specific, dynamically recalibrated authority boundaries to AI agents based on historical intervention outcomes, credentialed user activity, and one or more risk thresholds defined by institutional policy;

(c) a justification-capture module enforcing role-specific override grammars, analyzing override rationale, and detecting emerging intervention trends;

(d) a governance recorder that cryptographically chains and records, in a tamper-evident, chronologically ordered audit log, each AI decision, computed risk score, applied policy grammar, override rationale, and resulting policy or system adaptation for regulatory compliance and retrospective analysis;

(e) an omission-event governance engine configured to determine, using the policy grammar, that one or more required system actions have not been completed within a policy-defined time window and to generate a policy-defined omission event;

(f) a machine-implemented state-transition controller configured to suspend prescription dispensing, alert clearance, or authorization-state advancement until the governance recorder contains a cryptographically verifiable entry documenting completion of all policy-required system actions or an authorized override; and (g) a digital-signature verification engine configured to authenticate reviewer identity, role, and authorization prior to accepting any override, confirmation, or justification into the governance recorder;

wherein the modules operate synergistically such that policy grammars and credential boundaries are continuously and automatically updated in response to system-wide feedback and contextual signals, providing a technical improvement in secure healthcare data processing through traceable, policy-constrained, and tamper-resistant operation of an AI-driven prescription-monitoring system.

15. The system of claim 14, wherein the policy-constrained execution engine evaluates input data using a constraint grammar comprising dosage thresholds, refill intervals, and multiprovider conflict rules, wherein constraint grammar rules are dynamically adjusted based on realtime analysis of override feedback and population health trends, and said adjustments are immediately reflected in all subsequent alert generation and intervention workflows.

16. The system of claim 14, further comprising a trace replay engine for reconstructing, in real time, the decision path of each AI-generated alert, including all intermediate rule evaluations, policy branch resolutions, and system adaptation events, wherein authorized users may review the complete rationale for any intervention, including all cryptographically linked feedback and adaptation events.

17. The system of claim 14, wherein the justification capture module automatically analyzes override patterns and uses detected trends to proactively suggest new role-specific override grammars and policy templates, wherein such suggestions are subject to institutional approval and, once accepted, are cryptographically recorded and immediately operationalized by the policy-constrained execution engine.

18. The system of claim 14, further comprising a pathogen trend ingestion interface that, upon receiving a real-time outbreak signal from an external epidemiological intelligence platform, triggers system-wide updates in AI alert thresholds, policy grammars, and override justification formats, wherein all outbreak-driven adaptations, associated rationale, and subsequent intervention outcomes are cryptographically linked and auditable via the governance recorder.

19. The system of claim 1, wherein the AI engine tags alert records by patient demographic, insurance class, or geographic region to detect prescription bias or access inequity, wherein observed patterns of divergent override behavior across prescriber classes or patient demographic segments are automatically analyzed, and the analytics logic is updated in real time to surface emerging inequities, with all updates and analyses recorded for compliance review.

20. The system of claim 1, further comprising a public health alert syndication layer transmitting anonymized surveillance signals to external agencies or dashboards based on aggregate bias, outbreak, or behavioral trends, wherein analytic thresholds and reporting logic are dynamically adjusted in response to both internal feedback and external public health requirements, and all outgoing data, analytic changes, and reporting events are cryptographically recorded and auditable through the governance trace module.

* * * * *